(12) United States Patent
Dubois et al.

(10) Patent No.: US 7,734,133 B2
(45) Date of Patent: Jun. 8, 2010

(54) HOLLOW CORE WAVEGUIDE FOR LASER GENERATION OF ULTRASONIC WAVES

(75) Inventors: Marc Dubois, Keller, TX (US); Thomas E. Drake, Jr., Fort Worth, TX (US); Mark A. Osterkamp, Weatherford, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 12/121,559

(22) Filed: May 15, 2008
(Under 37 CFR 1.47)

(65) Prior Publication Data

US 2009/0285523 A1 Nov. 19, 2009

(51) Int. Cl.
| | |
|---|---|
| G02B 6/26 | (2006.01) |
| G02B 6/42 | (2006.01) |
| G02B 6/32 | (2006.01) |
| G01N 9/24 | (2006.01) |
| G01N 29/00 | (2006.01) |
| G01H 11/00 | (2006.01) |
| G01N 24/00 | (2006.01) |
| G01N 29/04 | (2006.01) |

(52) U.S. Cl. .............. 385/38; 385/31; 385/33; 73/643; 73/649; 73/570; 73/618; 73/620

(58) Field of Classification Search .................. 385/31, 385/32; 73/596, 649, 570, 655, 601, 618, 73/620, 627, 653, 628, 644, 633, 657, 643; 356/357, 352, 358, 359, 360, 349

See application file for complete search history.

(56) References Cited

U.S. PATENT DOCUMENTS

| | | | | | |
|---|---|---|---|---|---|
| 4,927,231 | A | * | 5/1990 | Levatter | ................. 385/31 |
| 5,137,361 | A | * | 8/1992 | Heon et al. | ................. 356/502 |
| 5,457,997 | A | * | 10/1995 | Naruo et al. | ................. 73/643 |
| 5,951,543 | A | * | 9/1999 | Brauer | ................. 606/10 |
| 6,122,060 | A | * | 9/2000 | Drake, Jr. | ................. 356/502 |
| 6,176,135 | B1 | * | 1/2001 | Dubois et al. | ................. 73/643 |
| 2005/0025965 | A1 | | 2/2005 | Sanghera | |

OTHER PUBLICATIONS

"Laser-based ultrasonic inspection with a fiber-coupled scanning Cassegrain system," by McKie et al, Ultrasonics, vol. 40, 2002, pp. 1037-1046.*

(Continued)

*Primary Examiner*—Frank G Font
*Assistant Examiner*—Robert Tavlykaev
(74) *Attorney, Agent, or Firm*—Bracewell & Giuliani LLP

(57) ABSTRACT

A laser transmission system is used for inspecting workpieces. The system has a source of laser beams that is coupled to a first lens assembly. A first hollow core waveguide is operably coupled to the first lens assembly. An end of an optical fiber coupled to the first hollow core waveguide. A second hollow core waveguide is coupled to the other end of the optical fiber. A second lens assembly operably coupled to the second hollow core waveguide. The length of the hollow core waveguides range from about 5 to 100 times the focal lengths of the lens assemblies. A motion control system is operably coupled to the second hollow core waveguide and the second lens assembly for controllably displacing the second hollow core waveguide and the second lens assembly with respect to a workpiece.

18 Claims, 2 Drawing Sheets

OTHER PUBLICATIONS

"Laser-ultrasound detection systems: a comparative study with Rayleigh waves," by Murfin et al, Measurement Science and Technology, vol. 11, 2000, pp. 1208-1219.*

International Search Report and Written Opinion for PCT/US/2009/043997 dated Nov. 18, 2009, 13 pages.

* cited by examiner

HOLLOW CORE WAVEGUIDE FOR LASER GENERATION OF ULTRASONIC WAVES

BACKGROUND

This disclosure relates to transmission systems for transmitting laser beams.

DETAILED DESCRIPTION

Figure 1:
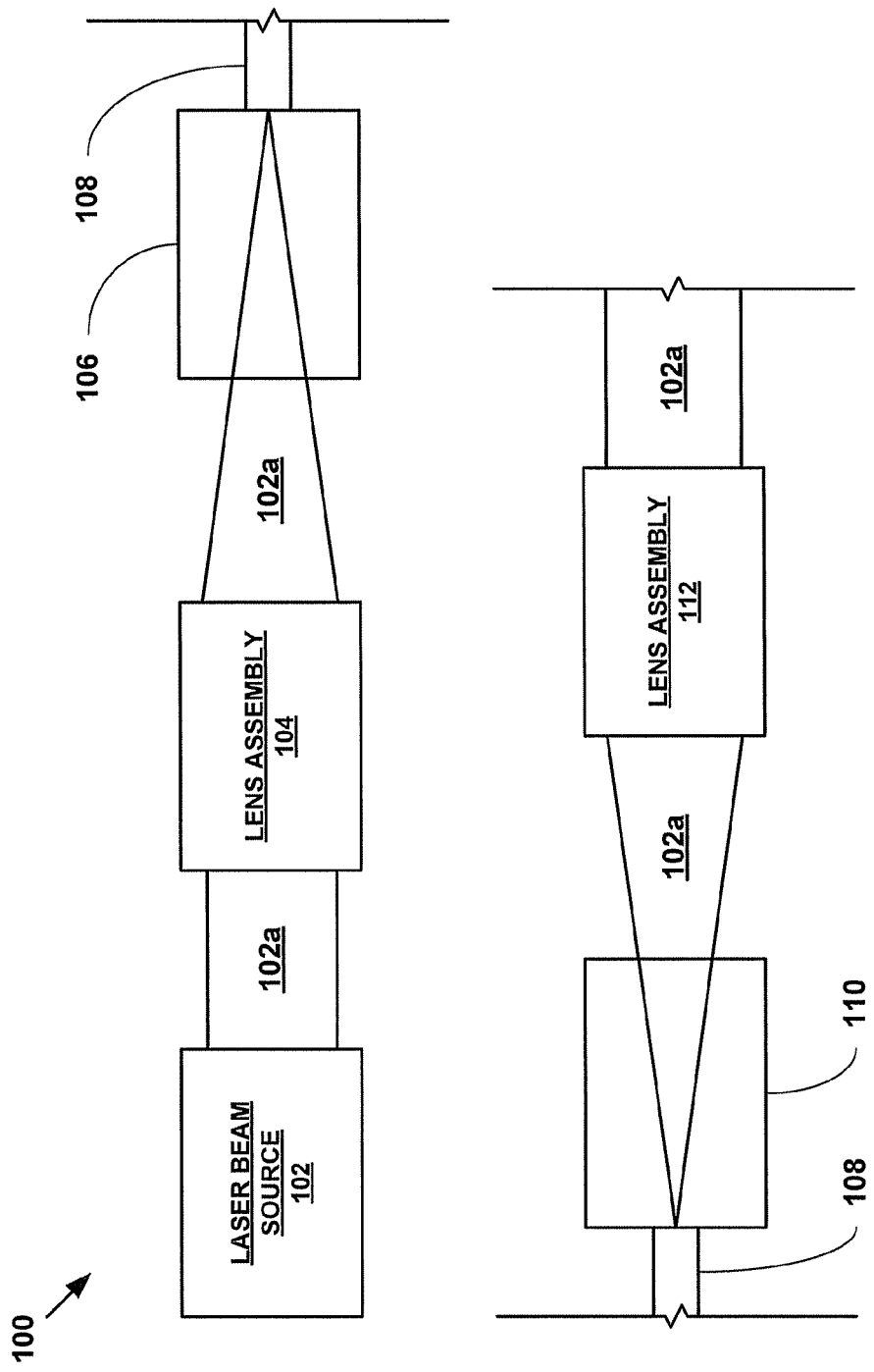
FIG. 1 is a schematic illustration of an exemplary embodiment of a laser transmission system.

In the drawings and description that follows, like parts are marked throughout the specification and drawings with the same reference numerals, respectively. The drawings are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results. The various characteristics mentioned above, as well as other features and characteristics described in more detail below, will be readily apparent to those skilled in the art upon reading the following detailed description of the embodiments, and by referring to the accompanying drawings.

Referring initially to FIG. 1, an exemplary embodiment of laser transmission system 100 includes a laser beam source 102 having an output that is operably coupled to the input of a lens assembly 104. The output of the lens assembly 104 is operably coupled to the input of a first hollow core waveguide 106. The output of the first hollow core waveguide 106 is coupled to an end of an optical fiber 108. The other end of the optical fiber 108 is coupled to input of a second hollow core waveguide 110. The output of the second hollow core waveguide 110 is operably coupled to the input of a lens assembly 112.

In an exemplary embodiment, the laser beam source 102 may be a conventional laser beam source such as, for example, a laser beam capable of generating wavelengths within the middle of the infra red region such as, for example, in the 3 to 5 micron range. In an exemplary embodiment, the lens assemblies, 104 and 112, may be conventional lens assemblies suitable for focusing a laser beam. In an exemplary embodiment, the hollow core waveguides, 106 and 110, may be conventional hollow core waveguides such as, for example, metal, plastic and glass hollow core waveguides. In an exemplary embodiment, the diameter of the hollow core waveguides, 106 and 110, are significantly greater than the diameter of the optical fiber 108. In an exemplary embodiment, the diameter of the hollow core waveguides, 106 and 110, are larger than the diameter of the beam 102a at the ends of the hollow core waveguides positioned in opposing relation to the lens assemblies, 104 and 112, respectively, taking into account the length of the hollow core waveguides and the numerical aperture and diameter of the optical fiber 108. In an exemplary embodiment, the lengths of the hollow core waveguides, 106 and 112, are significant relative to the focal lengths of the lens assemblies, 104 and 112, such that the diameter of the laser beam 102a is significantly larger at the ends of the hollow core waveguides versus at the ends of the optical fiber 108.

In an exemplary embodiment, during the operation of the system 100, the laser beam source 102 generates a laser beam 102a that is then focused by the lens assembly 104. The focused laser beam 102a then passes into the hollow core waveguide 106 and enters into and through the end of the fiber 108. At the other end of the end of the fiber 108, the laser beam 102a exits and passes into and through the hollow core waveguide 110. As the laser beam 102a passes through and out of the hollow core waveguide, the laser beam spreads and is then focused by the lens assembly 112.

Figure 2:
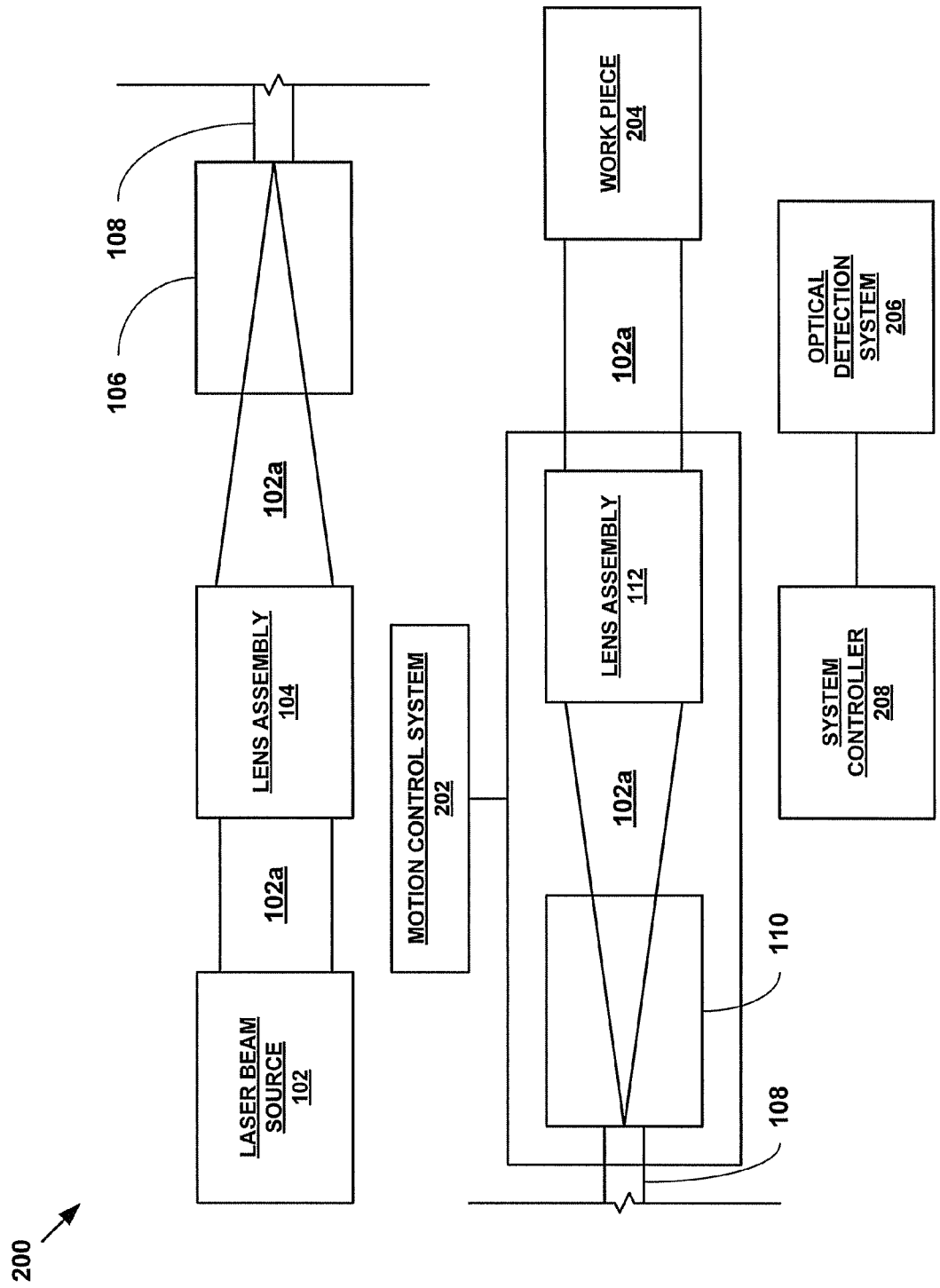
FIG. 2 is a schematic illustration of an exemplary embodiment of a laser ultrasound detection system that incorporates the laser transmission system of FIG. 1.

Referring now to FIG. 2, in an exemplary embodiment, the system 100 is incorporated into a laser ultrasound system 200 in which the hollow core waveguide 110 and lens assembly 112 are operably coupled to a motion control system 202 for controllably moving the hollow core waveguide and lens assembly relative to a work piece 204. A conventional optical detection system 206 is also provided proximate the work piece 204 that is operably coupled to a system controller 208. In an exemplary embodiment, the motion control system 202 may include, for example, a robotic arm.

In an exemplary embodiment, during the operation of the laser ultrasound system 200, the system 100 is operated by the system controller 208 to focus the laser beam 102a onto the surface of the work piece 204. In an exemplary embodiment, during the operation of the system 200, the motion control system 202 may be operated to position and orient the hollow core waveguide 110 and lens assembly 112 relative to one or more exterior surfaces of the work piece 204. Optical energy reflected by the exterior surfaces of the work piece 204 is then detected by the optical detection system 206 and processed by the system controller 208 in a well known manner to inspect the workpiece 204. The design and operation of using laser beam energy for laser ultrasound inspection of a work piece is considered well known to persons having ordinary skill in the art.

It is understood that variations may be made in the above without departing from the scope of the invention. Further, spatial references are for the purpose of illustration only and do not limit the specific orientation or location of the structure described above. While specific embodiments have been shown and described, modifications can be made by one skilled in the art without departing from the spirit or teaching of this invention. The embodiments as described are exemplary only and are not limiting. Many variations and modifications are possible and are within the scope of the invention. Accordingly, the scope of protection is not limited to the embodiments described, but is only limited by the claims that follow, the scope of which shall include all equivalents of the subject matter of the claims.

The invention claimed is:

1. A system for transmitting laser beams, comprising:
   a source of laser beams;
   a first lens assembly operably coupled to the source of laser beams for receiving laser beams from the source and focusing the laser beams;
   a first hollow core waveguide having a first end operably coupled to an output of the first lens assembly for receiving the focused laser beams;

a first end of an optical fiber coupled to a second end of the first hollow core waveguide for receiving the laser beams after they pass through the hollow core waveguide;

a second hollow core waveguide having a first end coupled to a second end of the optical fiber for receiving the laser beams from the optical fiber;

a second lens assembly having a first end operably coupled to the second hollow core waveguide for receiving the laser beams after they pass through the second hollow core wave guide; wherein:

a length of the first hollow core waveguide and a focal length of the first lens assembly are selected such that a diameter of the laser beams entering the first waveguide is larger than an outer diameter of the optical fiber; and a length of the second hollow core waveguide is selected so that a diameter of the laser beams as they exit the second hollow core waveguide is greater than the outer diameter of the optical fiber.

2. The system of claim 1, wherein the source of laser beams comprises a source of laser beams having wavelengths in the range of 3 to 5 microns.

3. The system of claim 1, wherein a refractive index of at least one of the first and second hollow core waveguides is substantially the same as a refractive index of the optical fiber.

4. The system of claim 1, wherein a length of at least one of the first and second hollow core waveguides ranges from about 5 to 100 times a focal length of at least one of the first and second lens assemblies.

5. The system of claim 1, further comprising a motion control system operably coupled to the second hollow core waveguide and the second lens assembly for controllably displacing the second hollow core waveguide and the second lens assembly with respect to a workpiece and with respect to the source of laser beams, the first lens assembly, and the first hollow core waveguide.

6. A method of transmitting a laser beam from a laser beam source to a work piece, comprising:

focusing the laser beam using a first lens assembly; then transmitting the laser beam from the first lens assembly into and through a first hollow core waveguide;

then transmitting the laser beam from the first hollow core waveguide into and though an optical fiber, and selecting a length of the first hollow core waveguide and a focal length of the first lens assembly such that a diameter of the laser beam entering the first waveguide is larger than an outer diameter of the optical fiber;

then transmitting the laser beam out of the optical fiber into and though a second hollow core waveguide; and then focusing the laser beam as it passes from the second hollow core waveguide using a second lens assembly, and selecting a length of the second hollow core waveguide so that a diameter of the laser beam as it exits the second hollow core waveguide is greater than the outer diameter of the optical fiber.

7. The method of claim 6, wherein the laser beam source comprises a source of laser beams having wavelengths in the range of 3 to 5 microns.

8. The method of claim 6, wherein a refractive index of at least one of the first and second hollow core waveguides is substantially the same as a refractive index of the optical fiber.

9. The method of claim 6, wherein a length of at least one of the first and second hollow core waveguides ranges from about 5 to 100 times a focal length of at least one of the first and second lens assemblies.

10. The method of claim 6, further comprising controllably displacing the second hollow core waveguide and the second lens assembly with respect to a workpiece and with respect to the laser beam source, the first lens assembly and the first hollow core waveguide.

11. A laser ultrasound system, comprising:

a source of laser beams;

a first lens assembly operably coupled to the source of laser beams for receiving and focusing laser beams from the source of laser beams;

a first hollow core waveguide operably coupled to the first lens assembly for receiving the focused laser beams from the first lens assembly;

an end of an optical fiber coupled to the first hollow core waveguide for receiving laser beams from the first hollow core waveguide;

a second hollow core waveguide coupled to the other end of the optical fiber for receiving laser beams from the optical fiber;

a second lens assembly operably coupled to the second hollow core waveguide for receiving and focusing laser beams from the second hollow core waveguide onto a work piece;

a motion control system operably coupled to the second hollow core waveguide and the second lens assembly for controllably positioning the second hollow core waveguide and the second lens assembly with respect to the work piece and relative to the source of laser beams, the first lens assembly and the first hollow core waveguide;

an optical detection system positioned proximate the work piece for detecting optical energy reflected off the work piece as a result of the focused laser beams striking the work piece;

a controller operably coupled to the source of laser beams, the motion control system, and the optical detection system for controlling the operation of the source of laser beams, the motion control system, and the optical detection system and for processing the optical energy reflected off the work piece to determine one or more characteristics of the work piece; wherein:

a length of the first hollow core waveguide and a focal length of the first lens assembly are selected such that a diameter of the laser beams entering the first waveguide is larger than an outer diameter of the optical fiber; and a length of the second hollow core waveguide is selected so that the diameter of the laser beams as they exit the second hollow core waveguide is greater than the outer diameter of the optical fiber.

12. The system of claim 11, wherein inner diameters of the first and second hollow core waveguides are greater than the outer diameter of the optical fiber.

13. The system of claim 11, wherein:

an inner diameter of a first end of the first hollow core waveguide is larger than the diameter of the laser beams where they enter the first end of the first hollow core waveguide; and an inner diameter of a second end of the second hollow core waveguide is larger than the diameter of the laser beams as they exit the second end of the second hollow core waveguide.

14. A method of determining one or more characteristics of a work piece, comprising:

generating a laser beam;

focusing the laser beam using a first lens assembly;

then transmitting the focused laser beam into and through a first hollow core waveguide; then transmitting the laser beam from the first hollow core waveguide into and through an optical fiber, and selecting a length of the first hollow core waveguide and a focal length of the first lens assembly such that a diameter of the laser beam entering the first waveguide is larger than an outer diameter of the optical fiber;

then transmitting the laser beam out of the optical fiber and into a second hollow core waveguide, and selecting a length of the second hollow core waveguide so that a diameter of the laser beam as it exits the second hollow core waveguide is greater than the outer diameter of the optical fiber;

then focusing the laser beam exiting the second hollow core waveguide using a second lens assembly;

controllably displacing the second hollow core waveguide and the second lens assembly with respect to the work piece and with respect to the first lens assembly and the first hollow core waveguide;

impacting one or more surfaces of the work piece with the laser beam exiting the second lens assembly;

monitoring reflection of the laser beam off one or more surfaces of the work piece; and processing the monitored reflections to determine one or more characteristics of the work piece.

15. The method of claim 14, wherein the laser beam source comprises a source of laser beams having wavelengths in the range of 3 to 5 microns.

16. The method of claim 14, wherein a refractive index of at least one of the first and second hollow core waveguides is substantially the same as a refractive index of the optical fiber.

17. The method of claim 14, wherein a length of at least one of the first and second ranges from about 5 to 100 times a focal length of at least one of the first and second lens assemblies.

18. The method of claim 14, further comprising controllably displacing the second hollow core waveguide and the second lens assembly with respect to a workpiece.

* * * * *